US008835668B2

(12) United States Patent
Hook et al.

(10) Patent No.: US 8,835,668 B2
(45) Date of Patent: Sep. 16, 2014

(54) PROCESS FOR THE PREPARATION OF INTERMEDIATES FOR THE MANUFACTURE OF NEP INHIBITORS

(75) Inventors: David Hook, Rheinfelden (CH); Jianguang Zhou, Suzhou (CN); Yunzhong Li, Suzhou (CN)

(73) Assignee: Novartis AG, Basel (CH)

( * ) Notice: Subject to any disclaimer, the term of this patent is extended or adjusted under 35 U.S.C. 154(b) by 17 days.

(21) Appl. No.: 13/818,507

(22) PCT Filed: Aug. 22, 2011

(86) PCT No.: PCT/EP2011/064410
§ 371 (c)(1),
(2), (4) Date: Feb. 22, 2013

(87) PCT Pub. No.: WO2012/025501
PCT Pub. Date: Mar. 1, 2012

(65) Prior Publication Data
US 2013/0158285 A1    Jun. 20, 2013

(30) Foreign Application Priority Data
Aug. 23, 2010 (WO) ............... PCT/CN2010/076245

(51) Int. Cl.
*C07C 209/68* (2006.01)
*C07C 269/06* (2006.01)

(52) U.S. Cl.
CPC ................................... *C07C 269/06* (2013.01)
USPC ......................................................... 560/27

(58) Field of Classification Search
CPC ............................ C07C 271/22; C07C 269/06
USPC .................................................... 560/19, 27
See application file for complete search history.

(56) References Cited

U.S. PATENT DOCUMENTS

| | | |
|---|---|---|
| 3,896,149 A | 7/1975 | Kotone |
| 5,102,882 A | 4/1992 | Kimura |
| 5,217,996 A | 6/1993 | Ksander |
| 5,250,522 A | 10/1993 | Lombaert |
| 5,273,990 A | 12/1993 | De Lombaert |
| 5,371,233 A | 12/1994 | Daumas et al. |
| 5,412,102 A | 5/1995 | Clark et al. |
| 5,550,119 A | 8/1996 | De Lombaert et al. |
| 6,043,265 A | 3/2000 | Murugesan et al. |
| 6,420,415 B1 | 7/2002 | Yamashita |
| 8,115,016 B2 | 2/2012 | Baker et al. |
| 8,580,974 B2 | 11/2013 | Hook et al. |
| 2003/0171578 A1 | 9/2003 | Iizuka |
| 2009/0326066 A1 | 12/2009 | Hook |
| 2012/0142916 A1 | 6/2012 | Hook |
| 2012/0289710 A1 | 11/2012 | Hook |
| 2013/0066101 A1 | 3/2013 | Hook |
| 2013/0158275 A1 | 6/2013 | Hook |

FOREIGN PATENT DOCUMENTS

| | | |
|---|---|---|
| EP | 0443983 B1 | 2/1991 |
| EP | 0555175 A1 | 1/1993 |
| EP | 0916656 A2 | 11/1998 |
| EP | 0885869 A1 | 12/1998 |
| EP | 1903027 | 3/2008 |
| FR | 2688503 A1 | 3/1992 |
| JP | 3056461 A2 | 3/1991 |
| WO | 03/059345 A1 | 7/2003 |
| WO | 03/082837 A1 | 10/2003 |
| WO | 2005/075462 A1 | 8/2005 |
| WO | 2005/107762 A2 | 11/2005 |
| WO | 2005/108409 A2 | 11/2005 |
| WO | 2006/016178 A1 | 2/2006 |
| WO | 2006/086456 A2 | 8/2006 |
| WO | WO 2008/031567 | 3/2008 |
| WO | WO2008/031567 * | 3/2008 |
| WO | 2008/083967 | 7/2008 |
| WO | 2008/138561 | 11/2008 |
| WO | 2009/090251 A2 | 7/2009 |
| WO | WO2009/090251 * | 7/2009 |
| WO | WO 2009/090251 | 7/2009 |

OTHER PUBLICATIONS

Ullrich et al. (Synthesis and Biological Evaluation of Pretubulysin and Derivatives, Eur. J. Org. Chem. pp. 6367-6378, 2009).*
DiFabio et al: 2002, "Novel Stereocontrolled Addition of Allylmental Reagents to r-Imino Ester: Efficient Synthesis of Chiral Tetrahydroquinoline Derivatives", J. Org. Chem. vol. 67, p. 7319-7328.
Oba et al:, 2006, "Convenient synthesis of deuterated glutamic acid, proline and leucine via catalytic deuteration of unsaturated pyroglutamate derivatives", J Label Compd Radiopharm, vol. 49, p. 229-235.
Ksander, et al: "Dicarboxylic acid dipeptide neutral endopeptidase inhibitors", Journal of Medicinal Chemistry, American Chemical Society, vol. 38, No. 10, pp. 1689-1700, 1995.
Database Caplus, Chemical Abstracts Service, Columbus, USA XP002438102 (2007).
Vicario et al: J. Org. Chem., vol. 66, pp. 5801-5807 (2001).
Clayton et al: Journal of the Chemical Society, Peptides Part V, pp. 371-380 (1956).
Sovjet Encyclopaedia M. 1988, vol. 1, p. 127.
DeLombaert et al: Bioorganic & Medicinal Chemistry Letters (1995) 5(2), pp. 145-150.
Knox et al: Journal of Medicinal Chemistry, 49,(22), pp. 6585-6590 2006.
Yin et al: Bioorganic & Medicinal Chemistry Letters, 16(1), 40-43 2006.

(Continued)

*Primary Examiner* — Brandon Fetterolf
*Assistant Examiner* — Blaine G Doletski
(74) *Attorney, Agent, or Firm* — Matthew Mulkeen

(57) ABSTRACT

The invention relates to a new process for producing useful intermediates for the manufacture of NEP inhibitors or prodrugs thereof, in particular NEP inhibitors comprising a γ-amino-δ-biphenyl-α-methylalkanoic acid, or acid ester, backbone, such as N-(3-carboxyl-1-oxopropyl)-(4S)-(p-phenylphenylmethyl)-4-amino-(2R)-methyl butanoic acid ethyl ester or salt thereof.

6 Claims, No Drawings

(56) References Cited

OTHER PUBLICATIONS

Hanessian et al: "The asymmetric synthesis of allylglycine and other unnatural alph-amino acids via zinc-mediated allylation of oximes in aqueous media#", Tetrahedron, 37(30): 5273-5276 (1996).
Katoh et al: "Synthetic studies on quinocarcin and its related compounds . . . " Tetrahedron 50(21): 6221-6238 (1994).
Dieterich et a: "Synthesis of (2S,3S)-[3-2H1]-4-methyleneglutamic acid and (2S,3R)-[2,3-2H2]-4methyleneglutamic acid", Organic & Biomolecular Chemistry, 2006, 4, 1492-1496.
Baker et al: "4-alkylidenyl glutamic acids, potent and selective gluR5 agonists", Bioorganic & Medicinal Chemistry Letters, 10 (2000) 1807-1810.
Blaser et al: "Selective hydrogenation for fine chemicals: recent trends and new developments", Adv. Synth. Catal. 2003, 345, Nos. !+2, pp. 103-151.
Ueno et al: "Deacylative condensation I. new facile method for the direct alpha-methylenation of ester or lactone starting from monosubstituted active methylene compounds" Tetrahedron Letters No. 39, pp. 3753-3756 (1978).
Riofsky et al: "Eploiting the facile release of trifluoracetate for the . . . ", The Journal of Organic Chemistry, 76 pp. 3676-3683 (Apr. 14, 2011).
Kan et al: "Stereocontrolled total synthesis of potent immunosuppressant FR901483", Organic Letters, 2004, 6(16): 2729-2731.

* cited by examiner

PROCESS FOR THE PREPARATION OF INTERMEDIATES FOR THE MANUFACTURE OF NEP INHIBITORS

NEW PROCESS

The invention relates to a new process for producing useful intermediates for the manufacture of NEP inhibitors or prodrugs thereof, in particular NEP inhibitors comprising a γ-amino-δ-biphenyl-α-methylalkanoic acid, or acid ester, backbone.

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP, EC 3.4.24.11), also responsible for e.g. the metabolic inactivation of enkephalins.

In the art biaryl substituted phosphonic acid derivatives are known which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals by inhibiting the degradation thereof to less active metabolites. NEP inhibitors are thus particularly useful for the treatment of conditions and disorders responsive to the inhibition of neutral endopeptidase (EC 3.4.24.11), particularly cardiovascular disorders such as hypertension, renal insufficiency including edema and salt retention, pulmonary edema and congestive heart failure.

Processes for preparing NEP-inhibitors are known. U.S. Pat. No. 5,217,996 describes biaryl substituted 4-amino-butyric acid amide derivatives which are useful as neutral endopeptidase (NEP) inhibitors, e.g. as inhibitors of the ANF-degrading enzyme in mammals. US 5 217 996 discloses the preparation of N-(3-carboxyl-1-oxopropyl)-(4S)-(p-phenylphenylmethyl)-4-amino-(2R)-methyl butanoic acid ethyl ester. In the preparation of said compound N-t-butoxycarbonyl-(4R)-(p-phenylphenylmethyl)-4-amino-2-methyl-2-butenoic acid ethyl ester is hydrogenated in the presence of palladium on charcoal. WO2009/090251 relates to a reaction route for preparing compound N-t-butoxycarbonyl(4S)-(p-phenylphenylmethyl)-4-amino-2-methylbutanoic acid ethyl ester, or salt thereof, wherein an alternative hydrogenation step provides improved diastereoselectivity compared to that obtained in U.S. Pat. No. 5,217,996. A key intermediate of the route described in WO2009/090251 is a compound of formula (1),

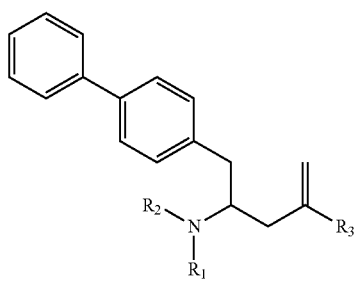

(1)

or salt thereof,
wherein R1 and R2 are, independently of each other, hydrogen or a nitrogen protecting group, and R3 is a carboxyl group or an ester group, preferably carboxyl group or alkyl ester.

According to WO2009/090251, a compound of formula (1) can be converted into a compound of formula (2), or salt thereof,

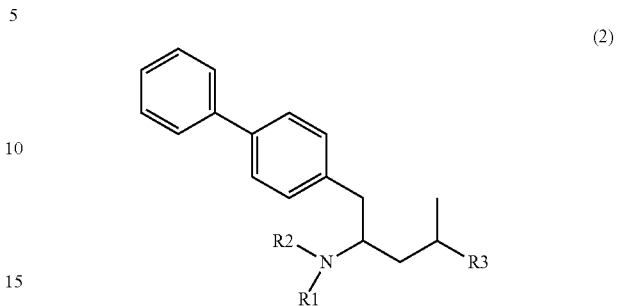

(2)

wherein R1 and R2 are, independently of each other, hydrogen or a nitrogen protecting group, and R3 is a carboxyl group or an ester group, preferably carboxyl group or alkyl ester. Compounds of formula (2) can be used as intermediates in the preparation of NEP inhibitors, or prodrugs thereof, in particular NEP inhibitors comprising a γ-amino-δ-biphenyl-α-methylalkanoic acid, or acid ester, backbone, preferably N-(3-carboxyl-1-oxopropyl)-(4S)-(p-phenylphenylmethyl)-4-amino-(2R)-methyl butanoic acid ethyl ester, for example, as described in the Journal of Medicinal Chemistry, 1995, 38, 1689.

The object of the present invention is to provide an alternative process for preparing NEP inhibitors or prodrugs thereof starting from a compound of formula (1), as described herein. The development of alternative routes to intermediates useful in the synthesis of pharmaceutical products provides means to find methods which are, for example, advantageous in an economic sense, from the technical point of view, or otherwise, in particular for large scale manufacture.

The new process, according to the present invention, for producing a compound according to formula (2), or salt thereof, as defined herein, is summarized in Scheme 1.

Scheme 1

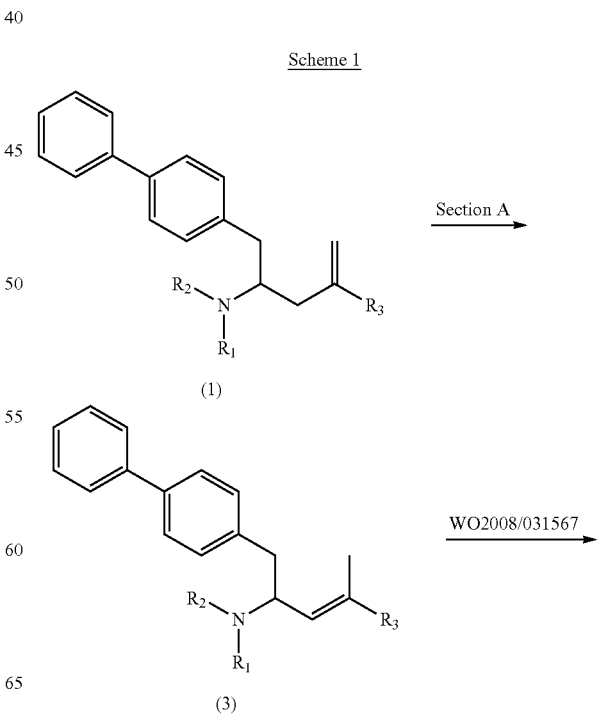

-continued

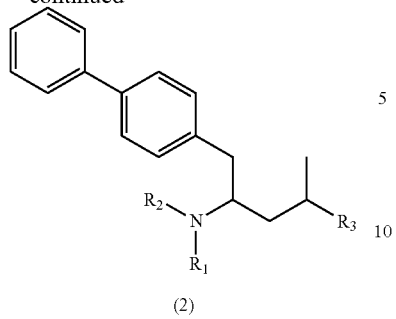

(2)

As shown in Scheme 1, a compound of formula (1), as described herein, is converted into a compound of formula (2), or salt thereof, wherein R1 and R2 are, independently of each other, hydrogen or a nitrogen protecting group, and R3 is a carboxyl group or an ester group, preferably carboxyl group or alkyl ester, according to a method which comprises the novel step described in Section A.

The invention as a whole comprises the following sections:
Section A: Conversion of a compound of formula (1) into a compound of formula (3)
Section B: Examples It is noted that in the present application usually explanations made in one section are also applicable for other sections, unless otherwise stated. When referring to compounds described in the present invention, it is understood that reference is also being made to salts thereof. Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms.

In a further embodiment, the present invention also relates to a process for preparing N-(3-carboxyl-1-oxopropyl)-(4S)-(p-phenylphenylmethyl)-4-amino-(2R)-methyl butanoic acid ethyl ester, or a salt thereof, comprising the manufacture of compound of formula (2), or salt thereof, as defined above, according to the method described herein. The process step described in Section A is also an embodiment of the present invention.

Section A: Conversion of a Compound of Formula (1) into a Compound of Formula (3)

The present invention relates to a process for preparing a compound of formula (3), or salt thereof, (3)

wherein
R1 and R2 are, independently of each other, hydrogen or a nitrogen protecting group, such as t-butoxycarbonyl (BOC); and R3 is a carboxyl group or an ester group, preferably a carboxyl group, said process comprising
reacting a compound of formula (1), or salt thereof,

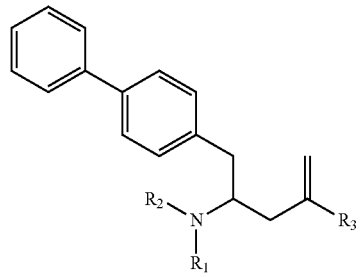

(1)

wherein R1 and R2 are, independently of each other, hydrogen or a nitrogen protecting group; and
R3 is a carboxyl group or an ester group, preferably a carboxyl group;
with a transition metal catalyst, optionally in the presence of a base,
to obtain the compound of formula (3), or salt thereof.

Suitable bases are, for example, an amine {eg diphenylamine, diisopropylamine, dimethylamine or imidazole, triethylamine, pyridine, 1,8-diazabicyclo[5.4.0]undec-7-ene (DBU), iPr$_2$EtN or 1,4-diazabicyclo[2.2.2]octane}, an alkali metal carbonate (eg sodium carbonate, potassium carbonate or cesium carbonate), an alkali earth metal carbonate (eg calcium carbonate, barium carbonate), an alkali metal hydrogen carbonate (eg NaHCO$_3$), an alkali metal hydroxide (eg sodium hydroxide, lithium hydroxide), or an alkali metal hydroxide (eg calcium hydroxide).

In a preferred embodiment, the present invention relates to a process for preparing a compound of formula (3a), or salt thereof, (3a)

wherein
wherein R1 and R2 are, independently of each other, hydrogen or a nitrogen protecting group, such as BOC; and
R3 is a carboxyl group or an ester group, preferably a carboxyl group.
said process comprising
reacting a compound of formula (1a), or salt thereof, (1a)

wherein R1 and R2 are, independently of each other, hydrogen or a nitrogen protecting group; and R3 is a carboxyl group or an ester group; preferably a carboxyl group; with a transition metal catalyst to obtain the compound of formula (3a), or salt thereof.

Suitable transition metal catalysts for the conversion of a compound of formula (1), preferably of formula (1a), as described herein, into a compound of formula (3), preferably of formula (3a), as described herein, include, for example, catalysts wherein the transition metal is selected from group 8, 9 or 10 of the periodic table. The transition metal catalyst comprises, for example, Ruthenium (Ru), Rhodium (Rh), Palladium (Pd) or Platinium (Pt); preferably the transition metal catalyst is palladium, such as Pd/C or Pd(Ph$_3$)$_4$. Further suitable transition metal catalysts are, for example, those described in Sections B.3.3, C.2 or D.4 in WO2009/090251, which are incorporated by reference herein.

General Terms

The general definitions used above and below, unless defined differently, have the following meanings:

The term "ester group" comprises any ester of a carboxyl group generally known in the art; for example groups —COOR, wherein R is selected from the group consisting of: $C_{1-6}$alkyl, such as methyl, ethyl or t-butyl, $C_{1-6}$alkoxy$C_{1-6}$alkyl, heterocyclyl, such as tetrahydrofuranyl, $C_{6-10}$aryloxy$C_{1-6}$alkyl, such as benzyloxymethyl (BOM), silyl, such as trimethylsilyl, t-butyldimethylsilyl and t-butyldiphenylsilyl, cinnamyl, allyl, $C_{1-6}$alkyl which is mono-, di- or trisubstituted by halogen, silyl, cyano or $C_{1-6}$aryl, wherein the aryl ring is unsubstituted or substituted by one, two or three, residues selected from the group consisting of $C_{1-7}$alkyl, $C_{1-7}$alkoxy, halogen, nitro, cyano and $CF_3$; or $C_{1-2}$alkyl substituted by 9-fluorenyl. In a preferred embodiment, the "ester group" is —COOR, wherein R is a $C_{1-6}$alkyl residue. In particular, R is methyl or ethyl.

The term "nitrogen protecting group" comprises any group which is capable of reversibly protecting a nitrogen functionality, preferably an amine and/or amide functionality. Preferably the nitrogen protecting group is an amine protecting group and/or an amide protecting group. Suitable nitrogen protecting groups are conventionally used in peptide chemistry and are described e.g. in the relevant chapters of standard reference works such as J. F. W. McOmie, "Protective Groups in Organic Chemistry", Plenum Press, London and New York 1973, in P. G. M. Wuts and T. W. Greene, "Greene's Protective Groups in Organic Synthesis", Fourth Edition, Wiley, N.J., 2007, in "The Peptides"; Volume 3 (editors: E. Gross and J. Meienhofer), Academic Press, London and New York 1981, and in "Methoden der organischen Chemie" (Methods of Organic Chemistry), Houben Weyl, 4th edition, Volume 15/I, Georg Thieme Verlag, Stuttgart 1974.

Preferred nitrogen protecting groups generally comprise: $C_1$-$C_6$-alkyl, preferably $C_1$-$C_4$-alkyl, more preferably $C_1$-$C_2$-alkyl, most preferably $C_1$-alkyl which is mono-, di- or tri-substituted by trialkylsilyl$C_1$-$C_7$-alkoxy (eg. trimethylsilyethoxy), aryl, preferably phenyl, or an heterocyclic group, preferably pyrrolidinyl, wherein the aryl ring or the heterocyclic group is unsubstituted or substituted by one or more, e.g. two or three, residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-C1-C2-alkoxycarbonyl (preferably phenyl-C1-C2-alkoxycarbonyl eg. benzyloxycarbonyl); $C_{1-10}$alkenyloxycarbonyl; $C_{1-6}$alkylcarbonyl (eg. acetyl or pivaloyl); $C_{6-10}$arylcarbonyl; $C_{1-6}$alkoxycarbonyl (eg. t-butoxycarbonyl); $C_{6-10}$aryl$C_{1-6}$alkoxycarbonyl; allyl or cinnamyl; sulfonyl or sulfenyl; succinimidyl group, silyl, e.g. triarylsilyl or trialkylsilyl (eg. triethylsilyl).

Examples of preferred nitrogen protecting groups are acetyl, benzyl, cumyl, benzhydryl, trityl, benzyloxycarbonyl (Cbz), 9-fluorenylmethyloxycarbony (Fmoc), benzyloxymethyl (BOM), pivaloyl-oxy-methyl (POM), trichloroethxoycarbonyl (Troc), 1-adamantyloxycarbonyl (Adoc), allyl, allyloxycarbonyl, trimethylsilyl, tert-butyl-dimethylsilyl, triethylsilyl (TES), triisopropylsilyl, trimethylsilylethoxymethyl (SEM), t-butoxycarbonyl (BOC), t-butyl, 1-methyl-1, 1-dimethylbenzyl, (phenyl)methylbenzene, pyrridinyl and pivaloyl. Most preferred nitrogen protecting groups are acetyl, benzyl, benzyloxycarbonyl (Cbz), triethylsilyl (TES), trimethylsilylethoxymethyl (SEM), t-butoxycarbonyl (BOC), pyrrolidinylmethyl and pivaloyl.

Examples of more preferred nitrogen protecting groups are pivaloyl, pyrrolidinylmethyl, t-butoxycarbonyl, benzyl and silyl groups, particularly silyl groups according to the formula SiR11R12R13, wherein R11, R12 and R13 are, independently of each other, alkyl or aryl. Preferred examples for R11, R12 and R13 are methyl, ethyl, isopropyl, t-butyl and phenyl.

Particularly preferred nitrogen protecting groups are pivaloyl and t-butoxycarbonyl (BOC).

Alkyl being a radical or part of a radical is a straight or branch (one or, if desired and possible, more times) carbon chain, and is especially $C_1$-$C_7$-alkyl, preferably $C_1$-$C_4$-alkyl.

The term "$C_1$-$C_7$-" defines a moiety with up to and including maximally 7, especially up to and including maximally 4, carbon atoms, said moiety being branched (one or more times) or straight-chained and bound via a terminal or a non-terminal carbon.

Cycloalkyl is, for example, $C_3$-$C_7$-cycloalkyl and is, for example, cyclopropyl, cyclobutyl, cyclopentyl, cyclohexyl and cycloheptyl. Cyclopentyl and cyclohexyl are preferred.

Alkoxy being a radical or part of a radical is, for example, $C_1$-$C_7$-alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$-$C_4$alkoxy is preferred.

Alkanoyl is, for example, $C_2$-$C_8$-alkanoyl and is, for example, acetyl [—C(=O)Me], propionyl, butyryl, isobutyryl or pivaloyl. $C_2$-$C_5$-Alkanoyl is preferred, especially acetyl.

Halo or halogen is preferably fluoro, chloro, bromo or iodo, most preferably, chloro, bromo, or iodo.

Halo-alkyl is, for example, halo-$C_1$-$C_7$alkyl and is in particular halo-$C_1$-$C_4$alkyl, such as trifluoromethyl, 1,1,2-trifluoro-2-chloroethyl or chloromethyl. Preferred halo-$C_1$-$C_7$alkyl is trifluoromethyl.

Alkenyl may be linear or branched alkyl containing a double bond and comprising preferably 2 to 12 C atoms, 2 to 10 C atoms being especially preferred. Particularly preferred is a linear $C_{2-4}$alkenyl. Some examples of alkyl groups are ethyl and the isomers of propyl, butyl, pentyl, hexyl, heptyl, octyl, nonyl, decyl, undecyl, dodecyl, tetradecyl, hexadecyl, octacyl and eicosyl, each of which containing a double bond. Especially preferred is allyl.

Alkylene is a bivalent radical derived from $C_{1-7}$alkyl and is especially $C_2$-$C_r$alkylene or $C_2$-$C_7$-alkylene and, optionally, can be interrupted by one or more, e.g. up to three, O, NR14 or S, wherein R14 is alkyl, each of which can be unsubstituted or substituted, by one or more substituents independently selected from for example, $C_1$-$C_7$-alkyl, $C_1$-$C_7$-alkoxy-$C_1$-$C_7$-alkyl or $C_1$-$C_7$-alkoxy.

Alkenylene is a bivalent radical derived from $C_{2-7}$alkenyl and can be interrupted by, one or more, e.g. up to three, O, NR14 or S, wherein R14 is alkyl, and is unsubstituted or substituted by one or more, e.g. up to three, substitutents preferably independently selected from the substitutents mentioned above for alkylene.

Aryl being a radical or part of a radical is, for example $C_{6-10}$aryl, and is, preferably a mono-or polycyclic, especially monocyclic, bicyclic or tricyclic aryl moiety with 6 to 10 carbon atoms, preferably phenyl, and which can be unsubstituted or substituted, by one or more substituents independently selected from for example, $C_1$-$C_7$alkyl, $C_1$-$C_7$-alkoxy-$C_1$-$C_7$-alkyl or $C_1$-$C_7$-alkoxy.

The term arylalkyl refers to aryl-$C_1$-$C_7$alkyl, wherein aryl is as defined herein and is for example benzyl.

The term carboxyl refers to —$CO_2H$.

Aryloxy refers to a Aryl—O—wherein aryl is as defined above.

Unsubstituted or substituted heterocyclyl is a mono- or polycyclic, preferably a mono-, bi- or tricyclic-, most preferably mono-, unsaturated, partially saturated, saturated or aromatic ring system with preferably 3 to 14 (more preferably 5 to 14) ring atoms and with one or more, preferably one to four, heteroatoms independently selected from nitrogen, oxygen, sulfur, S($=$O)- or S-($=$O)$_2$, and is unsubstituted or substituted by one or more, e.g. up to three, substitutents preferably independently selected from the group consisting of halo, $C_1$-$C_7$-alkyl, halo-$C_1$-$C_7$-alkyl, $C_1$-$C_7$-alkoxy, halo-$C_1$-$C_7$alkoxy, such as trifluoromethoxy and $C_1$-$C_7$-alkoxy-$C_1$-$C_7$-alkoxy. When the heterocyclyl is an aromatic ring system, it is also referred to as heteroaryl.

Acetyl is —C($=$O)$C_1$-$C_7$alkyl, preferably —C($=$O)Me.

Silyl is —SiRR'R", wherein R, R' and R" are independently of each other $C_{1-7}$alkyl, aryl or phenyl-$C_{1-4}$alkyl.

Sulfonyl is (unsubstituted or substituted) $C_1$-$C_7$-alkylsulfonyl, such as methylsulfonyl, (unsubstituted or substituted) phenyl- or naphthyl-$C_1$-$C_7$-alkylsulfonyl, such as phenylmethanesulfonyl, or (unsubstituted or substituted) phenyl- or naphthyl-sulfonyl; wherein if more than one substituent is present, e.g. one to three substitutents, the substituents are selected independently from cyano, halo, halo-$C_1$-$C_7$alkyl, halo-$C_1$-$C_7$-alkyloxy- and $C_1$-$C_7$-alkyloxy. Especially preferred is $C_1$-$C_7$-alkylsulfonyl, such as methylsulfonyl, and (phenyl-or naphthyl)-$C_1$-$C_7$-alkylsulfonyl, such as phenylmethanesulfonyl.

Sulfenyl is (unsubstituted or substituted) $C_{6-10}$aryl-$C_1$-$C_7$-alkylsulfenyl or (unsubstituted or substituted) $C_{6-10}$arylsulfenyl, wherein if more than one substituent is present, e.g. one to four substitutents, the substituents are selected independently from nitro, halo, halo-$C_1$-$C_7$alkyl and $C_1$-$C_7$-alkyloxy.

The term "catalyst" means any substance that affects the rate of a chemical reaction by lowering the activation energy for the chemical reaction.

The term "powder" means a catalyst having a water contain of from 0 to 30 mass %.

The term "substrate to catalyst ratio" (S/C) refers to the molar ratio of starting compounds, or salts thereof, to "transition metal catalyst".

The term "chiral" refers to molecules which have the property of non-superimposability on their mirror image partner, while the term "achiral" refers to molecules which are superimposable on their mirror image partner.

The term "tautomer" refers to, for example, enol-keto tautomers such as an aldehyde tautomer where such compounds can exists in either an enol or aldehyde form, or mixtures thereof.

In the formulae of the present application the term "∿∿" or "—" on a C-sp$^3$ represents a covalent bond wherein the stereochemistry of the bond is not defined. This means that the term "∿∿" or "—" on a C-sp$^3$ comprises an (S) configuration as well as an (R) configuration of the respective chiral centre. Furthermore, mixtures are also encompassed, e.g., mixtures of enantiomers, such as racemates, are encompassed by the present invention.

In the formulae of the present application the term "∿∿" on a C-sp$^2$ represents a covalent bond, wherein the stereochemistry or the geometry of the bond is not defined. This means that the term "∿∿" on a C-sp$^2$ comprises a cis (Z) configuration as well as a trans (E) configuration of the respective double bond. Furthermore, mixtures are also encompassed, e.g., mixtures of double bond isomers are encompassed by the present invention.

The compounds of the present invention can possess one or more asymmetric centers. The preferred absolute configurations are as indicated herein specifically.

In the formulae of the present application the term " ⁄ " on a C-sp$^3$ indicates the absolute stereochemistry, either (R) or (S).

In the formulae of the present application the term " ⁄ " on a C-sp$^3$ indicates the absolute stereochemistry, either (R) or (S).

In the formulae of the present application, the term "⸺" indicates a Csp$^3$-Csp$^3$ bond or a Csp$^2$-Csp$^2$ bond.

Salts are especially pharmaceutically acceptable salts or generally salts of any of the intermediates mentioned herein, where salts are not excluded for chemical reasons the skilled person will readily understand. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds or any of the intermediates mentioned herein with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane- sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, any of the intermediates mentioned herein may also form internal salts.

For isolation or purification purposes of any of the intermediates mentioned herein it is also possible to use pharmaceutically unacceptable salts, for example picrates or perchlorates.

In view of the close relationship between the compounds and intermediates in free form and in the form of their salts, including those salts that can be used as intermediates, for example in the purification or identification of the compounds or salts thereof, any reference to "compounds", "starting materials" and "intermediates" hereinbefore and hereinafter is to be understood as referring also to one or more salts thereof or a mixture of a corresponding free compound, intermediate or starting material and one or more salts thereof, each of which is intended to include also any solvate or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is not intended to exclude the plural, but only preferably means "one".

The term "prodrug," as used herein, represents in particular compounds which are transformed in vivo to the parent compound, for example, by hydrolysis in blood, for example as described in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996), and "The Organic Chemistry of Drug Design and Drug Action", $2^{nd}$ Edition, R B Silverman (particularly Chapter 8, pages 497 to 557), Elsevier Academic Press, 2004.

Prodrugs therefore include drugs having a functional group which has been transformed into a reversible derivative thereof. Typically, such prodrugs are transformed to the active drug by hydrolysis. As examples may be mentioned the following:

| Functional Group | Reversible derivative |
|---|---|
| Carboxylic acid | Esters, including e.g. alkyl esters |
| Alcohol | Esters, including e.g. sulfates and phosphates as well as carboxylic acid esters |
| Amine | Amides, carbamates, imines, enamines, |
| Carbonyl (aldehyde, ketone) | (mines, oximes, acetals/ketals, enol esters, oxazolidines and thiazoxolidines |

Prodrugs also include compounds convertible to the active drug by an oxidative or reductive reaction. As examples may be mentioned:

Oxidative activation
   N- and O- dealkylation
   Oxidative deamination
   N-oxidation
   Epoxidation
Reductive activation
   Azo reduction
   Sulfoxide reduction
   Disulfide reduction
   Bioreductive alkylation
   Nitro reduction.

Each of the above described reactions and/or reaction steps can be used individually or in combination in a method to prepare a NEP-inhibitor or a prodrug thereof, such as a NEP inhibitor or prodrug thereof comprising a γ-amino-δ-biphenyl-α-methylalkanoic acid, or acid ester, such as alkyl ester, backbone. In particular the NEP-inhibitor is N-(3-carboxy-1-oxopropyl)-(4S)-(p-phenylphenylmethyl)-4-amino-(2R)-methylbutanoic acid or a salt thereof or a prodrug thereof.

Section C: Examples

The following Examples serve to illustrate the invention without limiting the scope thereof, while they on the other hand represent preferred embodiments of the reaction steps, intermediates and/or the process of the present invention.

Abbreviations:
δ chemical shift
μl microliter
Ac acetyl
Bn benzyl
Boc tert-butoxycarbonyl
de diastereomeric excess
dr diastereomeric ratio
DMF=dmf N,N-dimethylformamide
DMSO dimethylsulfoxide
ee enantiomeric excess
ES electrospray
ESI electrospray ionisation
Et ethyl
EtOAc ethyl acetate
EtOH ethanol
h hour(s)
HNMR proton nuclear magnetic resonance
$HCl_{(aq)}$ hydrogen chloride aqueous solution
HPLC high performance liquid chromatography
iPr isopropyl
IR infra red
L liter
LC-MS liquid chromatography-mass spectrometry
M molarity
$MgSO_4$ magnesium sulfate
m/e mass-to-charge ratio
Me methyl
MeOH methanol
mg milligram
min minute(s)
ml milliliter
mmol(s) millimole(s)
mol(s) mole(s)
MS mass spectrometry
$N_2$ nitrogen
nm nanometer
NMR nuclear magnetic resonance
Ph phenyl
ppm parts per million
RT=rt room temperature
tBu tertiary-butyl
TFA trifluoroacetic acid
THF tetrahydrofuran
TLC thin layer chromatography
$t_R$ retention time In quoting NMR data, the following abbreviations may be used: s, singlet; d, doublet; t, triplet; q, quartet; quint., quintet; m, multiplet.

(R)-5-Biphenyl-4-yl-4-tert-butoxycarbonylamino-2-methyl-pent-(E)-2-enoic acid

A mixture of (R)-5-Biphenyl-4-yl-4-tert-butoxycarbonylamino-2-methylenepentanoic acid (0.38 g, 1 mmol, Example 32 in WO 2009/090251), Pd(PPh$_3$)$_4$ (70 mg, 0.06 mmol), PPh$_3$ (31.5 mg, 0.12 mmol) and sodium bicarbonate (0.27 g, 3.2 mmol) in 10 mL xylene is heated to reflux, and stirred overnight to afford (R)-5-Biphenyl-4-yl-4-tert-butoxycarbonylamino-2-methyl-pent-(E)-2-enoic acid as determined by HPLC analysis. Spectroscopic data as reported in Example 1 in WO 2008/031567.

HPLC Method

Column: Eclipse XDB-C18; 150×4.6mm; 5 µm. Mobile Phase A (0.1% H$_3$PO$_4$) in water; Mobile Phase B (Acetonitrile). Gradient: 0 min (30% B); 8 min (95% B); 15 min (95% B). Flow rate: 1.00 ml min-1. Wavelength: 210 nm. Temperature: 30 ° C.

Retention time: 8.2 min

The invention claimed is:

1. A process for preparing a compound of formula (3), or salt thereof, wherein

R1 and R2 are, independently of each other, hydrogen or a nitrogen protecting group, such as BOC; and R3 is a carboxyl group or an ester group, preferably a carboxyl group, said process comprising reacting a compound of formula (1), or salt thereof, (1)

wherein R1 and R2 are, independently of each other, hydrogen or a nitrogen protecting group; and R3 is a carboxyl group or an ester group, preferably a carboxyl group;

with a transition metal catalyst, optionally in the presence of a base, to obtain the compound of formula (3), or salt thereof.

2. A process according to claim 1, wherein the transition metal catalyst comprises Palladium (Pd).

3. A process according to claim 2, wherein the transition metal catalyst is Pd(PPh$_3$)$_4$.

4. A process according to claim 1, wherein

R1 is hydrogen;

R2 is BOC; and

R3 is a carboxyl group.

5. A process for preparing N-(3-carboxyl-1-oxopropyl)-(4S)-(p-phenylphenylmethyl)-4-amino-(2R)-methyl butanoic acid ethyl ester, or a salt thereof, comprising the manufacture of compound of formula (3), or salt thereof, as defined in claim 1.

6. A process for preparing N-(3-carboxyl-1-oxopropyl)-(4S)-(p-phenylphenylmethyl)-4-amino-(2R)-methyl butanoic acid, or a salt thereof, or a prodrug thereof, comprising the manufacture of compound of formula (3), or salt thereof, as defined in claim 1.

* * * * *